Figure 1:
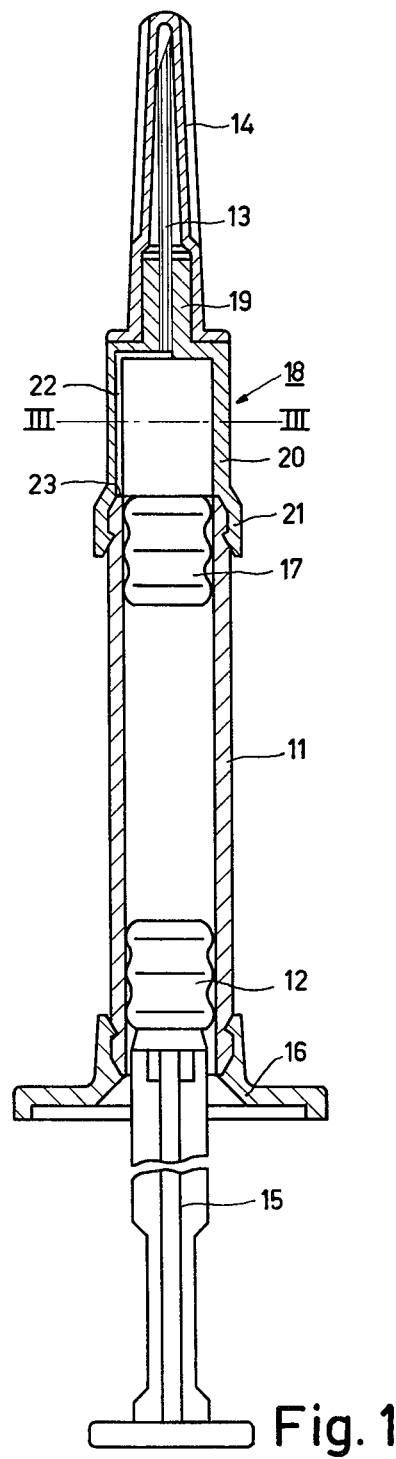

United States Patent [19]

Bekkering

[11] 4,235,235
[45] Nov. 25, 1980

[54] SYRINGE

[75] Inventor: Hendrik M. Bekkering, Olst, Netherlands

[73] Assignee: Duphar International Research B.V., Weesp, Netherlands

[21] Appl. No.: 968,642

[22] Filed: Dec. 11, 1978

[30] Foreign Application Priority Data

Dec. 23, 1977 [NL] Netherlands .......................... 7714308

[51] Int. Cl.³ ............................................. A61M 5/00
[52] U.S. Cl. ............................ 128/218 P; 128/218 D; 128/218 NV
[58] Field of Search ....... 128/218 P, 218 M, 218 NV, 128/218 R, 234, 215, 216, 220, 221

[56] References Cited

U.S. PATENT DOCUMENTS

| | | | |
|---|---|---|---|
| 3,330,282 | 7/1967 | Visser et al. ..................... | 128/218 M |
| 3,967,759 | 7/1976 | Baldwin et al. .................. | 128/218 M |
| 3,986,645 | 10/1976 | Baldwin et al. .................. | 128/218 P |
| 4,059,109 | 11/1977 | Tischlinger ...................... | 128/218 M |

Primary Examiner—John D. Yasko
Attorney, Agent, or Firm—Thomas A. Briody; Robert T. Mayer; Jack E. Haken

[57] ABSTRACT

The needle end of the barrel of a pre-filled syringe is sealed by a stopper which is displaceable into the shaft of a needle holder. The stopper is displaced, to release injection fluid, by operation of the syringe plunger. One or more slots in the walls of the needle holder shaft and the rear face of the needle holder neck conduct fluid around the displaced stopper. The stopper substantially fills the shaft of the needle holder but does not cover the ends of the slots which adjoin the barrel.

11 Claims, 6 Drawing Figures

SYRINGE

The invention relates to a syringe of the kind comprising a hollow, rotationally symmetric barrel which is open at both ends, a plunger which is movable in said barrel and seals same, a stopper whose dimensions are such that it will fit into the aperture at the front end of the barrel in a sealing manner, and a needle holder including a collar sealed on the front of the barrel, a neck in which or to which an injection needle is or can be attached in a sealing manner, the rear side of the needle not projecting beyond the rotationally symmetrical rear face of the neck, and a hollow shaft having a cylindrical interior which connects the collar to the neck in a sealing manner.

A syringe, of the aforesaid kind, and which is particularly intended and for single dosage use for transport and storage while filled with a liquid medicament and is disclosed in U.S. Pat. No. 3,941,128; it comprises a cylindrical barrel which, viewed in the direction in which the liquid is to be injected, comprises a fingergrip on the rear side and on the front side debouches into a kind of nozzle the inside diameter of which is considerable smaller than that of the remainder of the barrel. The collar of a needle holder is secured on the outside of said nozzle which collar is connected, via an internally hollow cylindrical shaft to a needle neck in which an injection needle is secured. On the rear side the cannula of the injection needle penetrates into the space enclosed by the rear wall of the neck and the inner wall of the shaft.

A stopper in the nozzle closes the nozzle completely. In the center, said stopper has a circular cross-section which corresponds approximately to a cross-section through the nozzle; it tapers at the front and rear ends and in addition comprises recesses there so that the front and the rear ends of the stopper are cross-shaped in cross-section.

When said syringe (which is filled with liquid medicine) is to be used a slight pressure is exerted on the plunger via a plunger rod so that the stopper is moved forward from the nozzle into the space enclosed by the shaft and the neck of the needle holder. When the syringe is held with the injection needle uppermost and the plunger is moved further forward and air will be expelled from the syringe. The injection needle can then be inserted into the patient and the liquid medicine present in the syringe injected by further forward movement of the plunger. The tapering cross-shaped ends of the stopper ensure that the stopper will not clog the entrance to the cannula when deaerating the syringe or injecting the liquid medicine.

It is known that a liquid in a pre-filled syringe can be sealed on the front side by means of a diaphragm which is perforated prior to using the injection needle. The disadvantage of such a construction, however, is that during the perforation small particles can be cut out of the diaphragm which may then clog the injection needle or enter the body of the patient.

This problem is avoided by constructing the syringe so that the diaphragm bursts under pressure. However, such a construction has the disadvantage that a considerable pressure has sometimes to be exerted to produce the bursting of the diaphragm; this may result in premature driving out of the injection liquid. The syringe according to U.S. Pat. No. 3,941,128 does not exhibit the this disadvantages because no diaphragm is present in said syringe there being used a stopper which is removed entirely from an aperture.

Sealing the front side of the barrel of a syringe on by means of a stopper which has to be removed prior to using the syringe has been suggested before. In some constructions the stopper, viewed in the direction in which the liquid is to be injected, has to be removed in a rearward direction from a closed aperture, either by pressing the injection needle or by moving the plunger rearwards (see for example, U.S. Pat. No. 2,798,487). Syringes which are constructed so that removal of the stopper is carried out by moving the plunger in the same direction in which it has to be moved for deaerating the syringe and for administering the injection are preferred, however. Such syringes are disclosed, for example, in the above-cited U.S. Pat. No. 3,941,128.

All syringes in which the barrel is closed by a stopper at the front end, have the disadvantage that a space behind the rear end of the injection needle for receiving the stopper is only partly filled by the stopper so as to enable the passage of air and liquid. After administering the injection, a rather large amount of liquid remains in this so-called dead space; the liquid being discarded together with the syringe. In particular in small syringes and/or with expensive liquid medicines, the dead space results in a considerable loss.

An additional disadvantage of the already suggested syringes equipped with a closing stopper is that they are complicated in shape and therefore expensive to manufacture; this applies in particular to the stopper in the above-mentioned U.S. Pat. No. 3,941,128. This is the more important because pre-filled syringes are manufactured in large numbers. Another disadvantage of a complicated shape of components of syringes is that these are difficult to clean before assembly so that the possibility of contamination of the injection liquid is increased. This applies in particular to the rubber components, such as the plunger and stopper. Rubber components are manufactured by cutting or punching so that said components always contain rubber particles. In contrast plastics components for this application are usually manufactured in dust-free circumstances (injection moulding) so that no separate plastics particles or dust particles are present.

It is the object of the invention to provide a syringe having a small dead space, a low resistance to flow of liquid during injection, a comparatively thick closing stopper so that little diffusion will occur, and components of a simple shape so that the cost of manufacture can be kept low.

This object is achieved with a syringe according to the invention in which the barrel has the shape of a hollow cylinder, the stopper has the shape of a cylinder whose outside diameter is slightly larger than the inside diameter of the barrel, the inner wall of the shaft and the rear face of the neck comprise one or more slots extending from the rear edge of the shaft to the rear end of the cannula or the neck aperture, and the space bounded by the inner wall of the shaft and the rear face of the neck, apart from the said slot or slots, has the same rotationally symmetrical but slightly longer shape and approximately the same diameter as the inside diameter of the barrel. The stopper can thus substantially fill said space but does not cover the part of the said slot or slots adjoining the barrel. The rearward directed end face of the stopper and the front face of the plunger are preferably both rotationally symmetric and complementary.

A further surprising aspect of the syringe of the present invention is that it is particularly suitable for a construction in two parts. The first part is formed by a barrel (with medicine) in which the stopper and the plunger are provided and which, if desired, already has a finger grip and/or a plunger rod. The second part of the syringe is formed by the needle holder or shaft and the needle connected thereto.

This construction in two parts has several advantages. It provides the user separate needle holders with needles of different dimensions, so that he can select the correct needle for each individual case. The barrel with medicine is supplied separately and is the only part of the syringe which may be restricted to a storage date and/or is to be subjected to a special treatment, for example post-sterilization, storage in the dark and/or while cooling. This is not only of advantage from a point of view of production but is also of importance for a more economical production method of the syringes.

In this construction the needle holder can be secured to the barrel in a simple manner, for example, by pressing the needle holder on the barrel (snap-cap construction) or screwing it on the barrel with a screw or bayonet joint. The syringe can also be more easily packaged because the separate parts are shorter. In addition, the sterilization of said individual parts is simpler and assembly in a sterile space can be reduced by one operation. Of course, the diameter and the connection means of the needle holder and barrel should be matched to each other.

The syringe of the present invention may also be used for dosing infusion liquids. In that case the needle holder is provided with a cap or shield, as described, for example, in U.S. Pat. No. 4,031,890 so that it cannot be used for intravenous injection. The same safety may also be obtained by using a thick plastics needle which is not suitable for an injection. In the above-mentioned application, aspiration is usually made impossible. This safety is achieved, for example, by not providing the plunger with a connection to the plunger rod. In the embodiment according to the present invention, the plunger may be identical to the stopper. In such an embodiment which is suitable only for infusion liquids, the barrel provided with the stopper and plunger is entirely symmetrical, which facilitates the assembly.

The needle holder of the syringe according to the present invention is also suitable for use in so-called two-chamber-syringes. For example, the syringe according to the invention, filled with a solvent for the medicament to be injected, may be detachably connected, by means of a telescopic assembly, to a vial containing the medicament; such a two-chamber-syringe is disclosed, for example, in applicant's Netherlands Patent Application No. 7,412,096. It will be obvious that the needle holder of the syringe according to the invention may also be used in two-chamber-syringes of a construction different from that described above.

Figure 3:
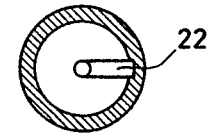
Figure 2:
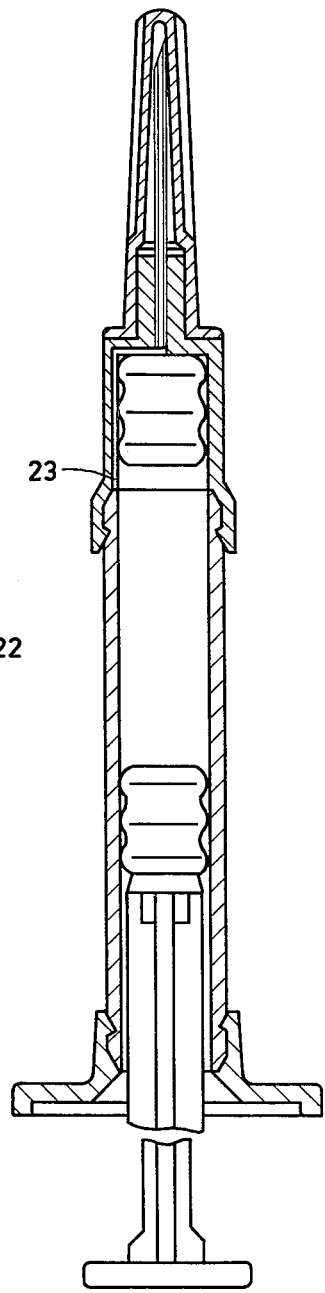
Figure 4:
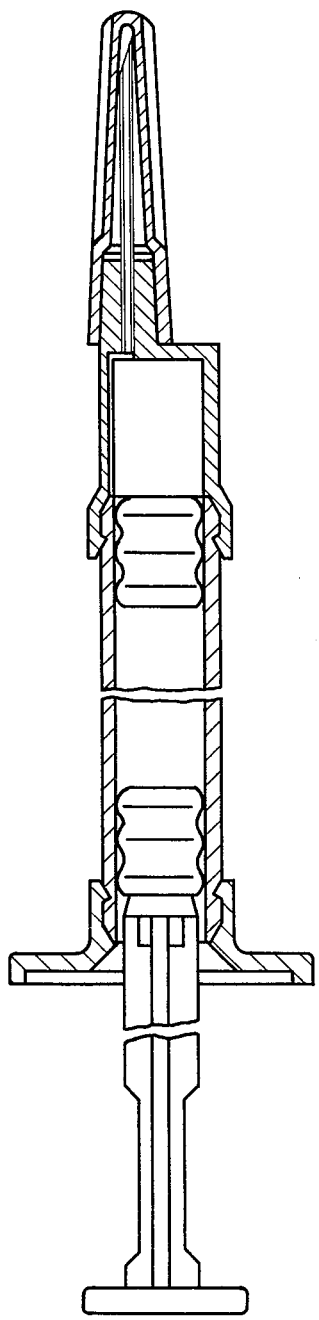
Figure 5:
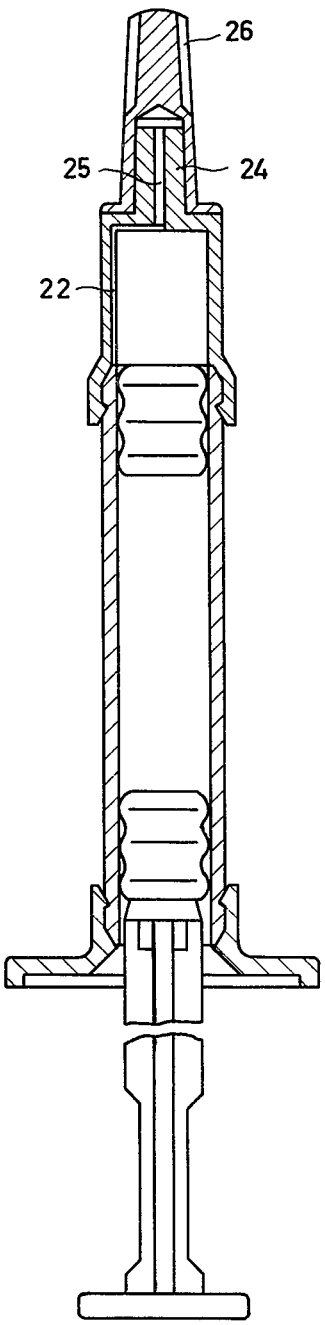
Figure 6:
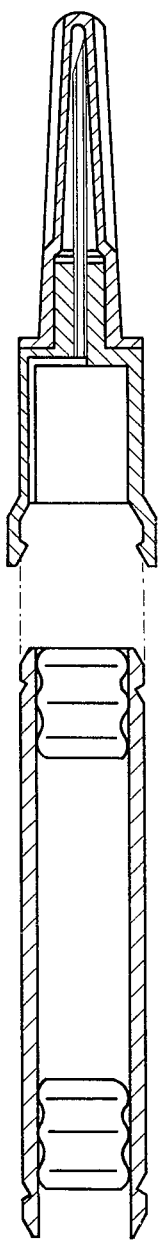

Embodiments of the invention will now be described in greater detail with reference to the drawings, in which FIG. 1 is a longitudinal sectional view of a syringe in a condition in which it can be transported and stored, FIG. 2 shows the syringe of FIG. 1 in a condition in which it is ready for administering an injection, FIG. 3 is a cross-sectional view through the needle holder of the syringe shown in the preceding Figures, taken on the line III—III of FIG. 1, viewed in the direction of the needle, and FIGS. 4, 5 and 6 are longitudinal sectional views of other embodiments of the invention.

The syringe shown in FIG. 1 comprises a barrel 11, in which a plunger 12 is provided on one end while the other end comprises an injection needle 13 surrounded by a needle-guard 14. The needle-guard 14 keeps the needle sterile during storage.

The plunger can be moved by means of a plunger rod 15 which is secured to the plunger, for example, by screwing. At the same end where the plunger is situated, the barrel has a fingergrip 16 which is secured to the barrel according to the so-called snap-cap principle. An alternate connection for a finger grip is disclosed in British Patent Specification No. 1,479,536 in the name of Applicants; the fingergrip described in said specification comprises a compressible collet which is clamped around the end of the barrel by means of a tightening sleeve. The fingergrip preferably consists of slightly resilient material, for example plastics. The barrel is manufactured from a rigid material, preferably glass. In another embodiment the fingergrip is a flangelike part of the barrel projecting radially outwards. Of course, other construction known to those skilled in the art are possible.

A stopper 17 which closes the barrel is situated in the end of the barrel remote from the plunger. The plunger and the stopper are manufactured from resilient material, preferably rubber of a pharmaceutical quality.

The injection needle 13 is secured to the barrel by means of a needle holder 18. The needle holder has a neck 19 which holds the needle, a shaft 20 and a collar 21. The needle holder is preferably manufactured from slightly resilient material which, however, has resistance to deformation for example, plastics and is secured to the end of the barrel by means of a snap-cap construction. In another embodiment the needle holder may be secured to the barrel by means of a screwed connection or, when the barrel also comprises a collar, by means of a clamping ring; in the latter embodiment the needle holder may also be flanged around a collar of the barrel.

One or more slots 22 are recessed in the inner wall of the shaft 20 and the rear face of the neck. This is shown in detail in FIG. 3 which is a cross-sectional view through the shaft of the needle holder taken on the line III—III of FIG. 1 and viewed in the direction of the needle. One slot is shown in FIG. 3 however more slots may be provided in the needle holder. The slot or slots extend into the rear end of the cannula. In cross-section the slots may be parts of a circle, as shown in FIG. 3, but other shapes are also possible, provided the size is such that sufficient injection liquid can be readily passed through; this is achieved if the diameter of the slot or the overall cross-section of the slots is at least as large as that of the cannula. The shaft of the needle holder is constructed so that when the stopper slides axially forward, it is received, with friction, by the shaft; therefore, apart from the slots recessed in the shaft, the inside diameter of the shaft is approximately as large as that of the barrel 11. The inside diameter of the shaft preferably is no larger than that of the barrel, so that during aspiration the stopper cannot be drawn back. The shaft of the needle holder is slightly longer than the stopper so that the part 23 of the slot(s) adjoining the barrel is free when the stopper is moved forward against the rear wall of the neck of the needle holder. This is shown clearly in FIG. 2 in which the syringe of FIG. 1 has been activated, that is, moved in the position in which it is ready for administering an injection. In this position the injection liquid can reach the cannula without hindrance via the slots. If desired, the needle protector may be constructed to also serve as a plunger rod. In that case, prior to the administration of an injection, the needle protector is removed from the needle and secured at the other end of the syringe to the plunger.

Generally, a syringe comprising a needle protector has a safety member which indicates whether the needle protector has previously been removed. Such a safety member in the form of a cap is described, for example, in applicants' Netherlands Patent Application No. 7,401,607.

In another embodiment, a longitudinal cross-sectional view of which is shown in FIG. 4, the needle is eccentric to the barrel. Such a construction is sometimes desired in syringes having a large barrel diameter.

In another embodiment, a longitudinal sectional view of which is shown in FIG. 5, the syringe is not stored with a needle in position. Before use, the needle is positioned on the neck 24 of the needle holder by means of a needle hub. A so-called Luer cone is preferably used for this connection. In this embodiment aperture 25 in the neck of the needle holder is closed on the outside by a protective cap 26 which ensures the sterility of the needle holder. Slot 22 recessed in the needle holder projects into the inner end of the neck aperture.

FIG. 6 shows a two part embodiment of the syringe. The needle holder with injection needle may also be constructed as a needle holder with a Luer cone; in that case the needle is supplied separately. The connection of needle holder to barrel is shown as a snap-cap construction. In a likewise efficacious construction each end of the barrel comprises a flange projecting radially outwards and forming one assembly with the barrel; on the rear side the flange forms a finger grip, on the front side it forms a connection for the needle holder. In order to facilitate dispensing, the barrel is preferably symmetrical on two sides.

The end face of the stopper directed rearwardly and the end face of the plunger directed forwardly are both preferably rotationally symmetrical and complementary in order to minimize the residual volume of medicine. In a further preferred embodiment of the syringe, both faces are substantially flat. In addition, the front face of the stopper and the rear face of the neck of the needle holder, apart from the slot or slots recessed in said rear face, are preferably flat surfaces; in this preferred embodiment of the syringe the quantity of medicine remaining in the syringe after the injection also is as small as possible.

The syringe embodying the present invention may also comprise a so-called "final filter" which serves to stop "particulate matter", if any, present in the injection liquid. Such a filter is preferably placed on the rear side in the duct in the neck of the needle holder, for example, in a cavity recessed for this purpose between the needle and the rear face of the neck.

What is claimed is:

1. A syringe comprising:
   a rotationally symmetrical barrel in the shape of a hollow cylinder with an open front end;
   a plunger, sealably disposed within said barrel and movable with respect thereto;
   a cylindrical stopper, having an outside diameter which is slightly larger than an inside diameter of the barrel and including means which seal the front end of the barrel; and
   a needle holder, including a collar which is attached in sealing relationship to the front end of the barrel, a neck for sealable attachment to an injection needle, the neck having a rotationally symmetric rear face which includes an aperture which functions to conduct fluid to the needle, and a hollow, internally cylindrical shaft having a rear end which is sealably connected to the collar and a front end which is sealably connected to the neck; wherein
   inner walls of the shaft and the rear face of the neck define one or more slots which extend from the rear end of the shaft to the aperture; and
   the space bounded by inner walls of the shaft and the rear face of the neck, apart from said slots, is longer than the stopper and has the same rotational symmetry and approximately the same diameter as the outer diameter of the stopper, so that the stopper can substantially fill the space but does not cover the ends of the slots at the rear end of the shaft.

2. A syringe as claimed in claim 1 wherein a rear face of the stopper is directed toward the plunger, a front face of the plunger is directed toward the stopper, and said faces are rotationally symmetrical and complementary.

3. A syringe as claimed in claim 1 further comprising a liquid medicament within the barrel and wherein the stopper is situated entirely within the barrel and seals the front end thereof.

4. A syringe as claimed in claim 1, 2 or 3 wherein a front face of the plunger is directed toward the stopper, a rear face of the stopper is directed toward the plunger, and said faces are both flat surfaces.

5. A syringe as claimed in claim 1, 2 or 3 wherein the barrel is detachable from the needle holder and includes: a plunger, a plunger rod adapted for connection to the plunger, and finger grip means; and wherein the syringe further includes means for connecting the barrel to the needle holder.

6. A syringe as claimed in claim 4, wherein the barrel is detachable from the needle holder and includes: a plunger, a plunger rod adapted for connection to the plunger, and finger grip means; and wherein the syringe further includes means for connecting the barrel to the needle holder.

7. A syringe as claimed in claim 1, 2 or 3 wherein a front face of the stopper faces the rear face of the neck, and wherein the rear face of the neck, apart form the slots recessed therein, and the front face of the stopper are both substantially flat surfaces.

8. A needle holder for a syringe which is adapted for connection to a barrel and which comprises:
   a collar;
   a neck for sealable connection to an injection needle, said neck having a rotationally symmetrical rear face which defines an aperture; and
   a hollow, internally cylindrical shaft having a rear end which is sealably connected to the collar and a front end which is sealably connected to the neck; wherein
   inner walls of the shaft and the rear face of the neck define one or more slots extending from the rear end of the shaft to the aperture; and
   the inside diameter of the shaft, apart from the slots, is approximately as large as an inside diameter of the barrel.

9. A needle holder as claimed in claim 8, further comprising a stopper having a front face which faces the rear face of the neck, wherein said front face of the stopper and the rear face of the neck, apart from the slots therein, are both substantially flat surfaces.

10. A syringe comprising:
   a needle holder as claimed in claim 8;
   a separate barrel including a stopper, a plunger, a plunger rod adapted for connection to the plunger, and finger grip means; and
   means which connect the separate barrel to the needle holder.

11. A syringe comprising:
   a needle holder as claimed in claim 9;
   a separate barrel including: a plunger, a plunger rod adapted for connection to the plunger, and finger grip means; and
   means which connect the separate barrel to the needle holder.

* * * * *